(12) United States Patent
Wang et al.

(10) Patent No.: US 9,408,694 B2
(45) Date of Patent: Aug. 9, 2016

(54) TIP FOR MEDICAL IMPLANT DELIVERY SYSTEM

(75) Inventors: Huisun Wang, Maple Grove, MN (US); Valerie J. Glazier, Eden Prairie, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 549 days.

(21) Appl. No.: 13/211,447

(22) Filed: Aug. 17, 2011

(65) Prior Publication Data

US 2012/0078237 A1 Mar. 29, 2012

Related U.S. Application Data

(60) Provisional application No. 61/374,435, filed on Aug. 17, 2010.

(51) Int. Cl.
*A61F 2/24* (2006.01)
*A61F 2/966* (2013.01)

(52) U.S. Cl.
CPC ............... *A61F 2/2436* (2013.01); *A61F 2/966* (2013.01)

(58) Field of Classification Search
CPC ............ A61M 25/0068; A61M 25/0069; A61M 25/008; A61M 2025/0073; A61M 2025/0687; A61M 25/0067; A61M 2025/0081
USPC .............. 623/2.11, 1.11, 1.12; 606/192–195; 604/96.01, 264
See application file for complete search history.

(56) References Cited

U.S. PATENT DOCUMENTS 5,102,417 A * 4/1992 Palmaz ..................... 606/195
5,603,698 A * 2/1997 Roberts ................. A61F 2/95
604/104

(Continued)

OTHER PUBLICATIONS

Australian Examination Report for Application No. 2011292463 dated Jul. 9, 2013.

(Continued)

*Primary Examiner* — Gregory Anderson
*Assistant Examiner* — Son Dang
(74) *Attorney, Agent, or Firm* — Lerner, David, Littenberg, Krumholz & Mentlik, LLP (57) ABSTRACT

A delivery system for delivering and deploying a medical implant, such as a prosthetic heart valve, includes an elongated support member, a sheath, and a tip. The sheath is movable relative to the elongated support member between a distal position overlying the medical implant and a proximal position exposing the medical implant for release from the delivery system. The tip is attached to the elongated support member and is positioned at a distal end of the sheath when the sheath is in the distal position. The tip has a compressed condition and an expanded condition, and a maximum diameter in the expanded condition that is larger than the outer diameter of the sheath.

13 Claims, 7 Drawing Sheets

(56) References Cited

U.S. PATENT DOCUMENTS

| | | | | |
|---|---|---|---|---|
| 5,662,700 | A * | 9/1997 | Lazarus | 606/194 |
| 5,876,436 | A | 3/1999 | Vanney et al. | |
| 6,719,790 | B2 | 4/2004 | Brendzel et al. | |
| 7,462,191 | B2 * | 12/2008 | Spenser et al. | 623/1.23 |
| 7,544,198 | B2 * | 6/2009 | Parodi | 606/139 |
| 8,414,632 | B2 * | 4/2013 | Kornkven Volk et al. | 623/1.11 |
| 2003/0144670 | A1 * | 7/2003 | Pavcnik et al. | 606/108 |
| 2003/0199849 | A1 * | 10/2003 | Hackett | 604/523 |
| 2004/0106900 | A1 * | 6/2004 | Triebes et al. | 604/104 |
| 2004/0236403 | A1 * | 11/2004 | Leonhardt et al. | 623/1.13 |
| 2006/0036263 | A1 * | 2/2006 | Stinson | 606/108 |
| 2006/0264905 | A1 * | 11/2006 | Eskridge et al. | 604/523 |
| 2007/0270780 | A1 * | 11/2007 | Venturelli | 604/526 |
| 2008/0015625 | A1 * | 1/2008 | Ventura et al. | 606/191 |
| 2008/0167522 | A1 * | 7/2008 | Giordano et al. | 600/104 |

OTHER PUBLICATIONS

International Preliminary Report on Patentabilty for Application No. PCT/US2011/001447 dated Feb. 19, 2013.
International Search Report for Application No. PCT/US2011/001447 dated Feb. 9, 2012.

* cited by examiner

TIP FOR MEDICAL IMPLANT DELIVERY SYSTEM

CROSS-REFERENCE TO RELATED APPLICATIONS

The present application claims the benefit of the filing date of U.S. Provisional Application No. 61/374,435, filed Aug. 17, 2010, the disclosure of which is hereby incorporated by reference herein.

BACKGROUND OF THE INVENTION

The present disclosure relates to medical implant delivery systems and methods and, more particularly, to delivery systems and methods for positioning an expandable prosthetic heart valve in a patient's vasculature.

Prosthetic heart valves are usually implanted in the human heart to replace natural valves. These valves essentially function as check valves, permitting the blood to flow through the valves in a downstream direction, but blocking blood flow in a reverse or upstream direction. Some prosthetic heart valves include an annular valve housing or body with a central orifice and occludes. The orifice provides a passageway for the blood, and the occludes open and close to regulate the passage of blood. For instance, U.S. Pat. Nos. 5,876,436 and 6,719,790 describe in detail specific prosthetic heart valves. Both of these references are hereby incorporated herein by reference in their entireties.

One type of prosthetic heart valve is collapsible to a relatively small circumferential size. This type of prosthetic heart valve can be delivered into a patient less invasively than valves that are not collapsible. For example, a collapsible valve may be delivered into the patient via a tube-like delivery apparatus such as a catheter, a tracer, a laparoscopic instrument, or the like. This can avoid the need for a more invasive procedure such as full open-chest, open-heart surgery. When the collapsed valve has reached the desired implant site in the patient (e.g., at or near the annulus of the patient's heart valve that is to be effectively replaced by the prosthetic valve), the prosthetic valve can be expanded to full operating size and released from the delivery apparatus. Typically, in its full operating size, the prosthetic valve engages adjacent native tissue of the patient to firmly anchor itself in the patient.

Because valves of the type described above are basically implanted by remote control (because the valve is inside the patient at the far end of delivery apparatus that is manipulated and controlled from its proximal end outside the patient), it can be difficult to get the valve to exactly the right location in the patient before releasing it from the delivery apparatus. Improvements are therefore sought with respect to how such valves are deployed.

One percutaneous delivery method entails introducing a collapsible prosthetic heart valve through a patient's femoral artery. This delivery method is referred to as a transfemoral approach. In transfemoral valve implantation, the collapsible prosthetic heart valve is delivered in a retrograde manner from the femoral artery through the aortic arch to, for example, the native aortic valve annulus.

Figure 1:
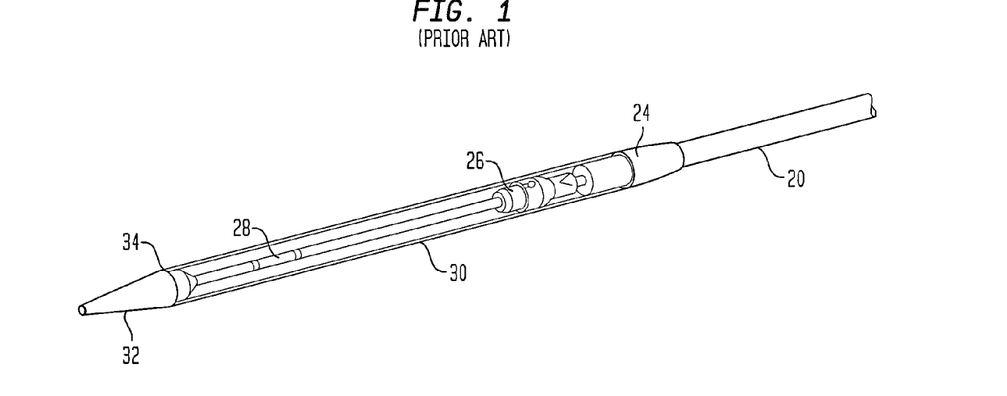
FIG. 1 is a perspective view of a distal portion of a conventional delivery system for collapsible prosthetic heart valves.
Figure 2:
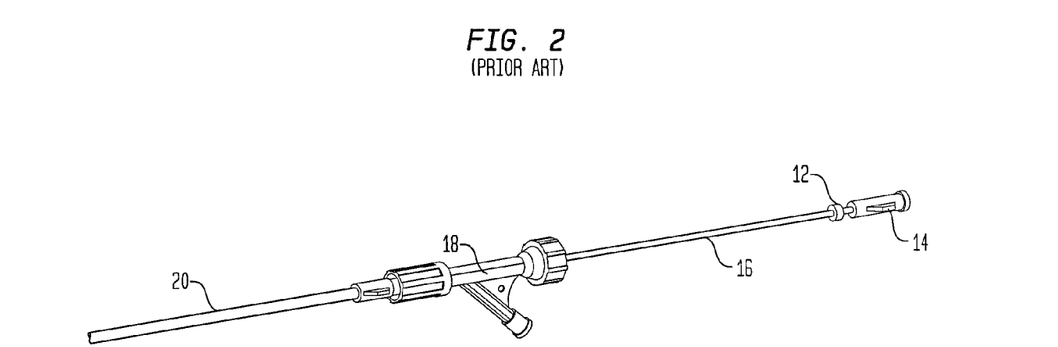
FIG. 2 is a perspective view of a proximal portion of the conventional delivery system of FIG. 1.

A delivery system and an introducer may be used to deliver the prosthetic heart valve to the native aortic valve annulus using the transfemoral approach. As seen in FIGS. 1 and 2, a conventional delivery system may include a distal sheath 30 for slidably enclosing a valve-containing compartment, and a proximal outer shaft 20 for controlling sliding movement of the distal sheath to open and close the compartment. The delivery system may further include a tip 32 having a maximum diameter that is substantially similar to the outer diameters of the distal sheath 30 and the proximal outer shaft 20. For example, in an 18F delivery system, the proximal outer shaft 20, the distal sheath 30, and the maximum diameter of the tip 32 are each about 18F. In such conventional delivery systems, the distal end 34 of the distal sheath 30 may be outwardly flared as a consequence of contacting the proximal surface of the tip 32. The flared distal end 34 of the distal sheath 30 may catch on body tissue as the delivery system is advanced in the patient's vasculature. For instance, the distal end 34 of the distal sheath 30 may catch on the aortic valve, the calcified aortic annulus, and/or lesions or calcified tissue in the aortic arch.

Figure 3:
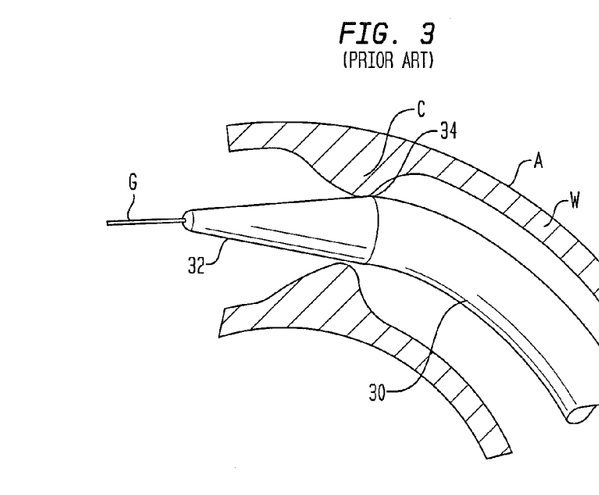
FIG. 3 is a highly schematic view of a distal portion of the delivery system of FIG. 1 located inside an aortic arch.

During transfemoral valve implantation, the distal sheath 30 of the delivery system is bent significantly to pass through the aortic arch A, which significantly biases the sheath toward the outside wall W of the aortic arch A, as illustrated in FIG. 3. Consequently, the flared distal end 34 of the distal sheath 30 may forcibly contact at least a portion of the outside wall W as the delivery system is advanced toward the native aortic valve annulus. The distal end 34 of the distal sheath 30 may also catch on calcified tissue C located on the outside wall W of the aortic arch A, as seen in FIG. 3. The contact between the distal sheath 30 and the outside wall W of the aortic arch A may cause various adverse effects on the patient. For instance, when the delivery system passes through the aortic arch A, the distal end 34 of the distal sheath 30 may damage the outside wall W of the aortic arch A, or may sever calcified tissue C, which may in turn cause an embolism. It is therefore desirable to minimize the contact between the distal sheath 30 and body tissue when advancing a delivery system using the transfemoral delivery approach.

BRIEF SUMMARY OF THE INVENTION

The present disclosure relates to a delivery system for delivering and deploying a medical implant, such as a prosthetic heart valve. The delivery system includes an elongated support member configured to hold a medical implant; a sheath having an outer diameter surrounding at least a portion of the elongated support member, the sheath being movable between a proximal position and a distal position relative to the elongated support member; and a tip attached to the elongated support member and positioned at a distal end of the sheath when the sheath is in the distal position, the tip having a compressed condition, an expanded condition, and a variable diameter along a length thereof. In the expanded condition, the maximum diameter of the tip is larger than the outer diameter of the sheath. The maximum diameter of the tip in the expanded condition may be about 0.005 inches to about 0.020 inches larger than the outer diameter of the sheath.

The tip may be made at least partly of a compressible material selected from the group consisting of polyether block amide, polyurethane, and silicone rubber. At least a first portion of the tip may have a first stiffness of a second portion of the tip.

In certain embodiments, the tip may have a closed inner cavity containing a fluid substance. The fluid substance may be selected from the group consisting of a liquid, a gel and a gas.

The tip may include an outer member formed from a porous material and an inner member formed from an elastic material. The outer member may surround at least a portion of the inner member. A plurality of longitudinal recesses may be formed along the length of the tip.

The tip may be formed by an injection molding process, including a multi-step injection molding process. The injection molding process may include an overmolding step. In such injection molding processes, the tip may be molded over a portion of the elongated support member.

BRIEF DESCRIPTION OF THE DRAWINGS

Various embodiments of the presently disclosed delivery system are disclosed herein with reference to the drawings, wherein.

DETAILED DESCRIPTION

Embodiments of the presently disclosed delivery systems are described herein in detail with reference to the drawings, wherein like reference numerals identify similar or identical elements. In the description which follows, the term "proximal" refers to the end of the delivery system, or portion thereof, which is closest to the operator, while the term "distal" refers to the end of the system, or portion thereof, which is farthest from the operator.

FIGS. 1 and 2 depict the distal and proximal portions, respectively, of a conventional delivery system for collapsible prosthetic heart valves. The delivery system includes an inner tube 16 having a guidewire lumen extending therethrough. A proximal hub 14 is disposed at the proximal end of the inner tube 16 and is adapted for connection to another system or mechanism, such as a handle, a syringe or other device for displacing the distal sheath 30. Mechanisms for displacing the distal sheath 30 are described in International Patent Application Publication No. WO/2009/091509, the entire contents of which are hereby incorporated herein by reference. A retention ring 12 may be disposed on the proximal end of the inner tube 16, distally of hub 14. At least a portion of the inner tube 16 extends through a Y-connector 18 and an outer shaft 20. The Y-connector 18 includes a hemostasis valve for preventing or at least minimizing blood flow between inner tube 16 and outer shaft 20. In addition, the Y-connector may be fluidly coupled to a fluid source.

As shown in FIG. 1, the outer shaft 20 extends to a transition member 24, which may have a tapered shape. Transition member 24 interconnects the distal end of the outer shaft 20 and the proximal end of the distal sheath 30. The distal sheath 30 surrounds a retainer 26 and the distal portion of a tubular support shaft 28 and can maintain a prosthetic heart valve supported on the support shaft 28 in a collapsed condition. The support shaft 28 is operatively connected to the inner tube 16. Retainer 26 is fixed on the support shaft 28 and is configured for supporting a prosthetic heart valve or any other suitable medical implant. Thus, the retainer 26 and at least a portion of the support shaft 28 can together hold a medical implant, such as a prosthetic heart valve. The distal sheath 30 is movable relative to the support shaft 28 between a distal position, shown in FIG. 1, for retaining a collapsed prosthetic heart valve in place during delivery to a target implant site, and a proximal position for uncovering the valve for deployment. A tip 32 is connected to the distal end of the support shaft 28. While FIGS. 1-3 depict a conventional tip 32 having a tapered profile, the present disclosure focuses on replacing this conventional tip with the tips illustrated in FIGS. 4-14.

Figure 4:
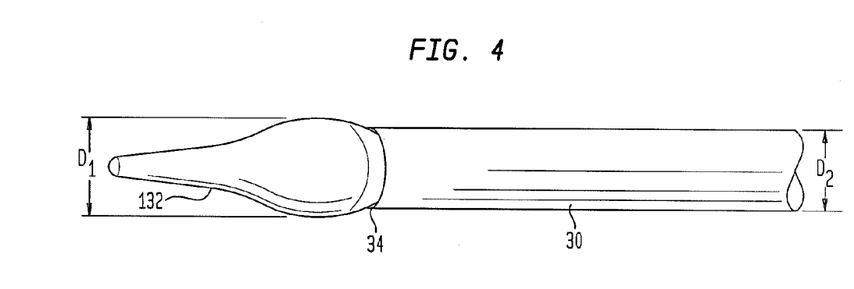
FIG. 4 is a perspective view of a distal portion of a delivery system for collapsible prosthetic heart valves according to an embodiment of the present invention.
Figure 5:
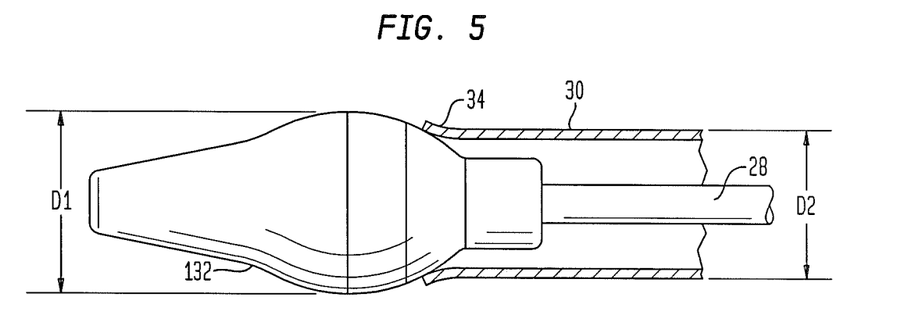
FIG. 5 is a side elevation of the distal portion of the delivery system of FIG. 4 in partial cross-section.

FIGS. 4 and 5 show a compressible tip 132 for use with the delivery system depicted in FIGS. 1-3. The tip 132 is made entirely or partly of a compressible material, such as a soft polymer, and may have a substantially conical shape to facilitate atraumatic insertion in a body lumen. Regardless of its particular shape, the diameter of the tip 132 varies along its length. As shown in FIGS. 4 and 5, the maximum diameter $D_1$ of the tip 132 is slightly larger than the outer diameter $D_2$ of the distal sheath 30. In certain embodiments, the maximum diameter $D_1$ of the tip 132 may be about 0.005 inches to about 0.020 inches larger than the outer diameter $D_2$ of the distal sheath 30. The difference in diameters between the tip 132 and the distal sheath 30 may prevent the distal end 34 of the distal sheath 30 from contacting the outside wall W of the aortic arch during delivery of the medical implant, as discussed in detail below.

Figure 6:
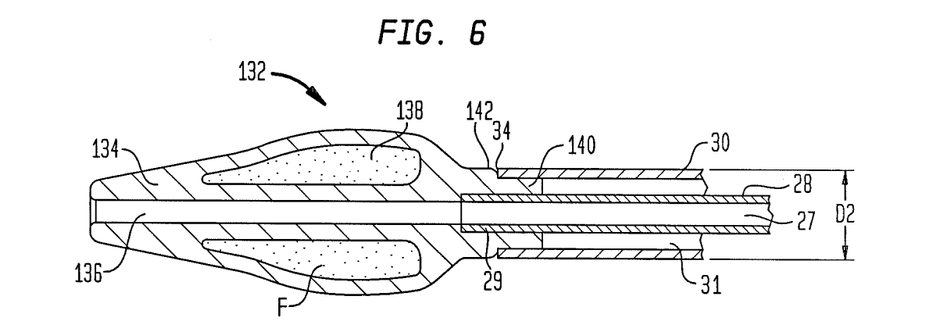
FIG. 6 is a side cross-sectional view of the distal portion of the delivery system of FIG. 4.

As shown in FIG. 6, one embodiment of the tip 132 may include a body 134 made of any suitable compressible material. For example, the body 134 of the tip may be entirely or partly formed of a soft elastic polymeric material, such as the polyether block amide sold under the trademark PEBAX® by Arkema France, a polyurethane, silicone rubber or any other suitable polymer.

Figure 14:
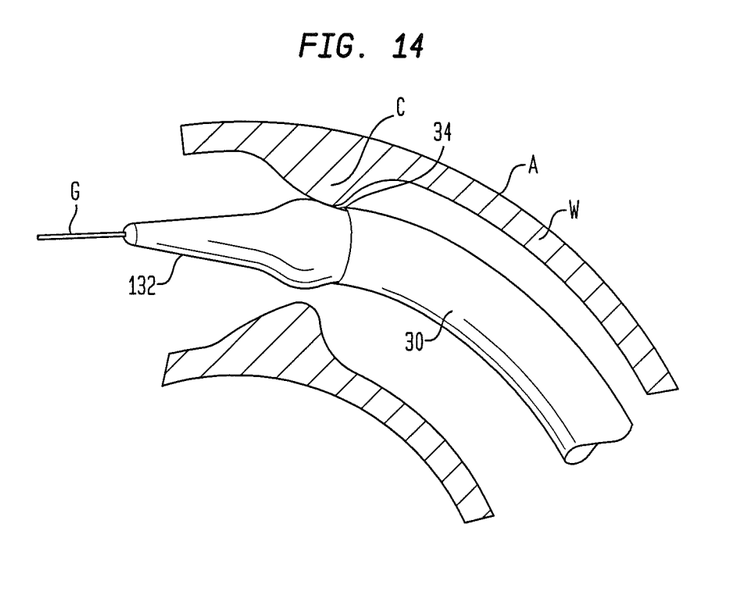
FIG. 14 is a highly schematic view of the distal portion of the delivery system of FIG. 4 positioned inside an aortic arch.

The body 134 of the tip 132 has a central lumen 136 extending therethrough. The lumen 136 extends along the entire length of the body 134 and is dimensioned to receive a guidewire G, as seen in FIG. 14. The body 134 of the tip 132 may further have a sealed inner cavity 138 surrounding at least a portion of the lumen 136. The inner cavity 138 may extend along substantially the entire length of the body 134, or only a portion thereof. For instance, in the embodiment depicted in FIG. 6, most of the inner cavity 138 is located at a proximal portion of the tip 132. The inner cavity 138 of the body 134 may have a frusto-conical shape and is configured to contain a fluid substance F, such as a liquid, gel, or gas. The fluid substance F allows the tip 132 to be compressed and, therefore, change its shape. When the fluid substance F is a liquid or a gel, the tip 132 can change its shape when subjected to compressive forces, but its volume will remain substantially constant. On the other hand, when the fluid substance F is a gas, the tip 132 can not only change its shape, but also its volume when subjected to compressive forces.

As seen in FIG. 6, the body 134 of the tip 132 has a generally annular proximal end portion 140 sized and shaped to be received within the lumen 31 of the distal sheath 30. The body 134 may further include a collar 142 located adjacent and distal to the proximal end portion 140. The diameter of the collar 142 may be substantially similar to or greater than the outer diameter $D_2$ of the distal sheath 30 to establish a fluid-tight seal with the distal end 34 of the distal sheath.

The support shaft 28 of the delivery system is attached at its distal end to the proximal end of the tip 132. The central lumen 27 of the support shaft 28 communicates with the lumen 136 in the body 134 so that guidewire G can extend through support shaft 28 and into and through tip 132. A distal portion 29 of the support shaft 28 may extend into the lumen 136 of the body 134 and may be held in place therein by compressive and frictional forces exerted by the material forming body 134.

Figure 7:
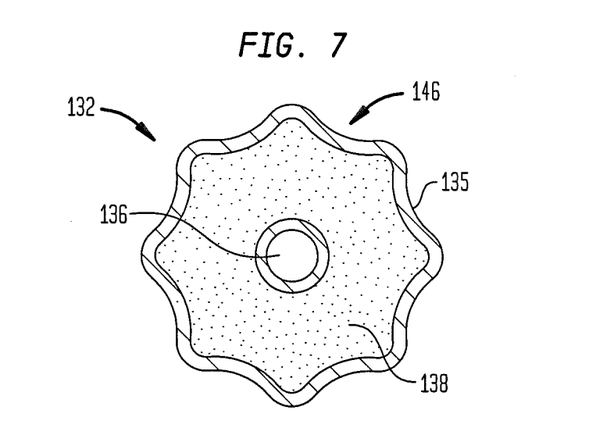
FIG. 7 is a rear cross-sectional view of a distal portion of a delivery system for collapsible prosthetic heart valves according to another embodiment of the present invention.

With reference to FIG. 7, the tip 132 may optionally have one or more longitudinal grooves or recesses 146 formed on the outer surface 135 of body 134. The longitudinal recesses 146 may extend along at least a portion of the length of the body 134 and facilitate radial compression of the tip by relieving pressure from the body during compression.

Figure 8:
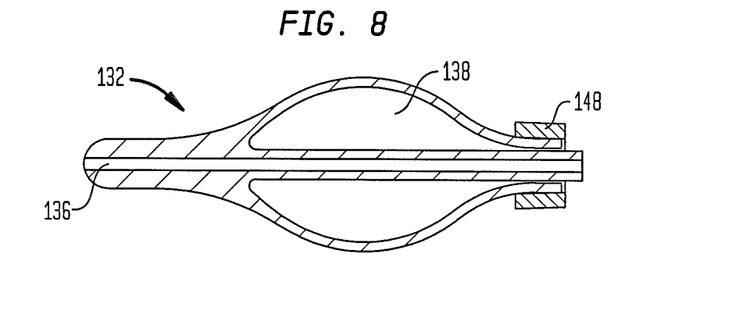
FIG. 8 is a side cross-sectional view illustrating a process for manufacturing the distal tip of the delivery system of FIG. 4.

The tip 132 may be made using various manufacturing methods. In one exemplary method schematically shown in FIG. 8, the tip 132 is manufactured as a one-piece molded component using an injection molding process. In one embodiment of this injection molding process, a suitable material, such as a thermoplastic polymer, is injected into a mold cavity having a shape substantially similar to the outer shape of the tip 132. The mold may include one or more inserts for forming the inner cavity 138 of the tip. After molding the inserts are removed, and a fluid substance, such as a liquid, gel, or gas, is injected into the inner cavity 138. A ring or collar 148 may then be assembled or molded over the proximal end of the molded tip 132 to close the inner cavity 138, thereby sealing the fluid substance in place. The collar 148 may later form the proximal end portion 140 of the tip body 134. The tip 132 may be attached to the distal end of the support shaft 28 using any suitable means, such as bonding the two together using adhesive, heat, ultrasonic welding and other techniques known in the art. Alternatively, the tip 132 may be molded directly over the distal end of the support shaft 28, such as through an overmolding process. In the event overmolding is employed, the distal end of the support shaft 28 may be inserted into a mold through a tube, and the tip 132 may then be molded over the support shaft.

Figure 9:
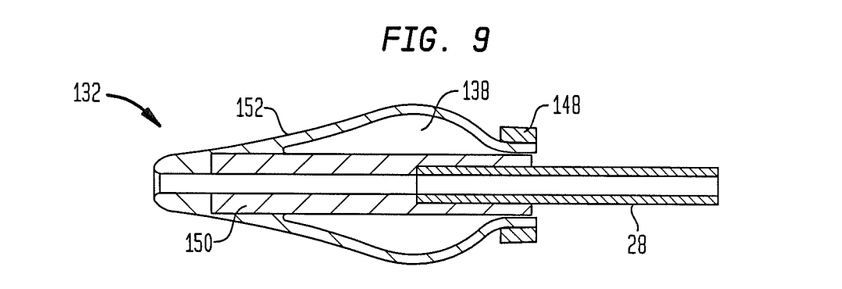
FIG. 9 is a side cross-sectional view illustrating another process for manufacturing the distal tip of the delivery system of FIG. 4.

With reference to FIG. 9, the tip 132 may also be manufactured as a two-piece molded structure using a multi-step sequential injection molding process. This sequential injection molding process entails overmolding. Overmolding processes mold a new layer over a previously molded part to allow the new layer to form around the existing part. In this exemplary manufacturing method, a support member 150 having a substantially cylindrical shape may be formed first by injecting any suitable material into an appropriately shaped mold cavity. After the molded support member 150 has completely cured, additional material may be injected around the molded support member 150 and one or more inserts to form the outer body 152 and cavity 138 around the support member. Alternatively, the outer body 152 may be molded separately and attached to the support member 150 using any suitable means, such as bonding with an adhesive, heat, ultrasonic welding and other techniques known to the skilled artisan. Once the tip 132 has been fully formed, a fluid substance, such as a liquid, gel, or gas, may be injected into the inner cavity 138. A collar or ring 148 may then be assembled or molded around the proximal end of the tip 132 to close the inner cavity 138, thereby sealing the fluid substance in place. The completed tip 132 may be attached to the distal end of support shaft 28 using any suitable process, such as the overmolding or bonding processes discussed above.

The injection molding processes described above may entail delivering the material into the mold cavity in a single shot. Alternatively, the injection step may include sequentially delivering multiple shots of the same or different materials to the mold cavity to form a tip 132 having different properties in different portions thereof. For example, the tip 132 may have a proximal portion formed of a first material and a distal portion formed of a second different material. The materials forming the proximal and distal portions may have different molding properties or different cured properties, such as stiffness or hardness. For instance, the material forming the proximal portion of the tip 132 may have a greater stiffness than the material forming the distal portion of the tip. The tip 132, however, should be sufficiently flexible to be able to follow a guidewire G through a patient's vasculature, as shown in FIG. 14.

Figure 10:
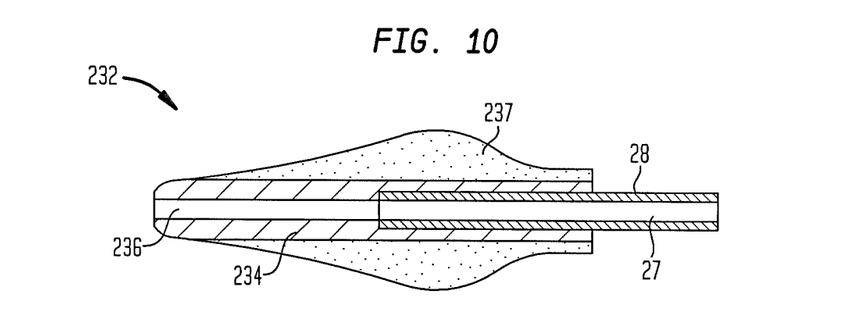
FIG. 10 is a side cross-sectional view of a distal portion of a delivery system according to a further embodiment of the present invention.

FIG. 10 shows a tip 232 in accordance with an alternate embodiment of the present invention. The tip 232 includes an inner member 234 made of an elastic material, such as a polymer. The inner member 234 may have a substantially cylindrical shape and is attached to the distal end of the support shaft 28. Regardless of its shape, the inner member 234 defines a lumen 236 extending therethrough which communicates with the lumen 27 of the support shaft 28 so that guidewire G can extend through both components. In some embodiments, at least a distal portion of the support shaft 28 is secured within the lumen 236 of the inner member 234. The tip 232 further includes an outer portion 237 surrounding at least a portion of the inner member 234. The outer portion 237 is entirely or partly made of any suitable porous material capable of absorbing liquids, such as blood or saline. Examples of suitable porous materials include, but are not limited to, porous polymers, including polyethylene, polypropylene and the like. The porous material of the outer portion 237 is compressible and less stiff or rigid than the elastic material forming the inner member 234. The outer portion 237 of the tip 232 is adapted to expand upon absorption of liquids, and therefore can expand as it absorbs blood during delivery of a medical implant, such as a prosthetic heart valve, as discussed in detail below.

Figure 11:
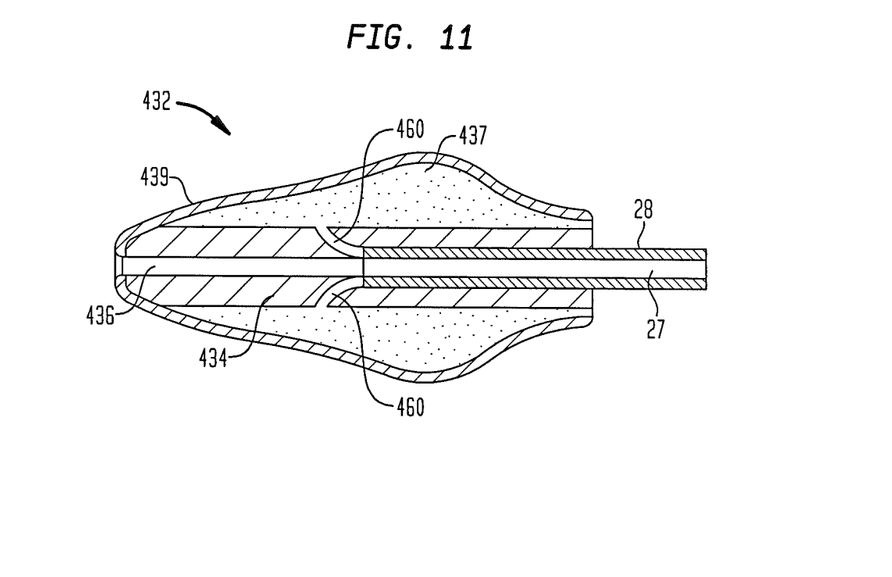
FIG. 11 is a side cross-sectional view of a distal portion of a delivery system according to yet another embodiment of the present invention.

FIG. 11 illustrates a tip 432 according to another embodiment of the invention that can be actively expanded during operation. The tip 432 includes an inner member 434 made of an elastic material, such as a polymer. The inner member 434 may have a substantially cylindrical shape and is attached to the distal end of support shaft 28. Further, the inner member 434 has a lumen 436 extending therethrough. At least a portion of the lumen 436 is in communication with the lumen 27 of the support shaft 28 so that guidewire G can extend through both components. In certain embodiments, at least a distal portion of the support shaft 28 is securely positioned within the lumen 436 of the inner member 434.

The tip 432 further includes an outer portion 437 formed entirely or partly of any suitable porous material capable of expanding upon absorption of a liquid. Examples of suitable porous materials include, but are not limited to, porous polymers, including polyethylene, polypropylene and the like. The porous material of the outer portion 437 is compressible and less stiff or rigid than the elastic material forming the inner member 434.

The outer portion 437 of the tip 432 is in fluid communication with a fluid source (not shown) via one or more tubes or conduits 460 extending from support shaft 28 and through inner member 434, and formed partly or entirely of an elastic material. More particularly, the support shaft 28 may have one or more channels (not shown) disposed in fluid communication with the conduits 460. These channels may extend along at least a portion of the length of the support shaft 28 and may be coupled at their proximal ends to a fluid source, such as a liquid, gel, or gas. In some embodiments, the support shaft 28 may have a single annular channel extending therealong and communicating with all conduits 460. The fluid source may contain any suitable fluid, such as saline. The porous material forming the outer portion 437 is configured to expand as it absorbs a fluid substance, such as saline, from the fluid source.

In addition to the outer portion 437, the tip 432 may include a thin outer layer 439 made of any suitable liquid-impermeable material, such as a polymer. The outer layer 439 surrounds the porous outer portion 437 and, therefore, seals liquids inside the outer portion of the tip.

Figure 12:
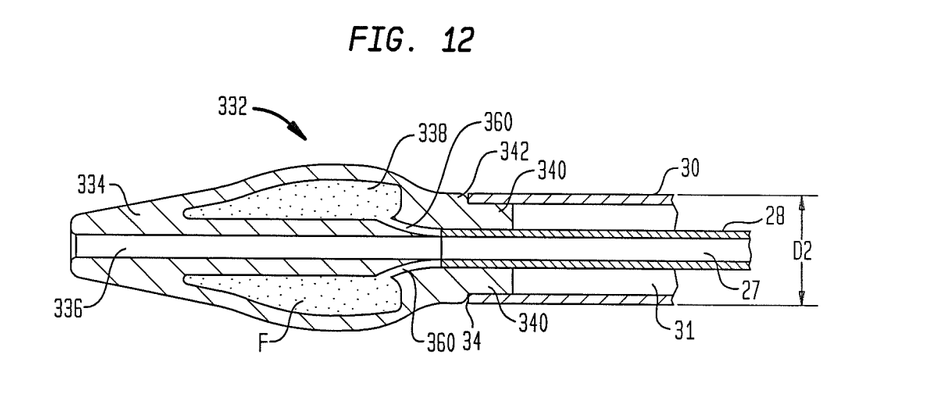
FIG. 12 is a side cross-sectional view of a distal portion of a delivery system according to a still further embodiment of the present invention.

FIG. 12 illustrates a tip 332 in accordance with another embodiment of the present invention. The tip 332 includes a body 334 made entirely or partly of a compressible material. The body 334 may have a substantially frusto-conical shape with a lumen 336 extending therethrough. The lumen 336 of the body 334 may have a substantially cylindrical shape and communicate with the lumen 27 of the support shaft 28 so that guidewire G can be passed therethrough. The body 334 further has an inner cavity 338 surrounding at least a portion of the lumen 336. In some embodiments, the inner cavity 338 may extend along only a portion of the length of the body 334. The inner cavity 338 of the body 334 may have a substantially frusto-conical shape similar to that of the body itself and is configured to receive and contain a fluid substance F, such as a liquid, gel, or gas. The fluid substance F allows the tip 332 to be compressed and, therefore, change its shape. When the fluid substance F is a liquid or a gel, the tip 332 can change its shape when subjected to compressive forces, but its volume will remain substantially constant. When the fluid substance F is a gas, on the other hand, the tip 332 can change not only its shape, but also its volume when subjected to compressive forces.

The body 334 of the tip 332 includes a generally annular proximal end portion 340 sized and shaped to be received within the lumen 31 of the distal sheath 30. The body 334 may further include a collar 342 located adjacent and distal to the proximal end portion 340. The diameter of the collar 342 may be substantially similar to or greater than the outer diameter $D_2$ of the distal sheath 30. Consequently, the collar 342 may create a fluid-tight seal with the distal end 34 of the distal sheath 30.

In the embodiment depicted in FIG. 12, the inner cavity 338 of the body 334 is in fluid communication with a fluid source via one or more conduits 360 extending from the support shaft 28 and formed partly or entirely from a flexible material. Aside from its central lumen 27, the support shaft 28 may have one or more channels (not shown) disposed in fluid communication with the conduits 360. These channels may extend along at least a portion of the length of the support shaft 28 and may be coupled at their proximal ends to a source of fluid, such as a liquid, gel, or gas. In one embodiment, the support shaft 28 may include a single annular channel in fluid communication with all of the conduits 360. The inner cavity 338 of the tip 332 is configured to expand when it receives a fluid substance F from this source of fluid via the conduits 360.

Figure 13A:
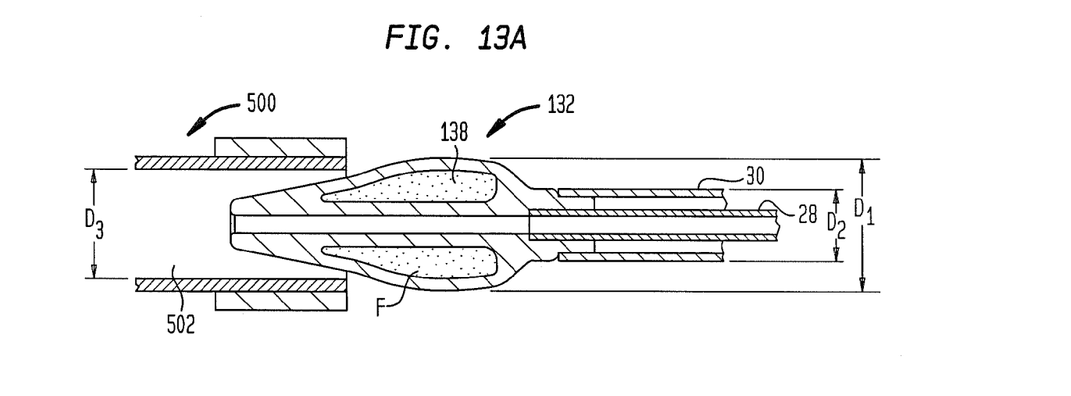
FIGS. 13A-13C are side cross-sectional views illustrating the method of using the delivery system of FIG. 4.
Figure 13B:
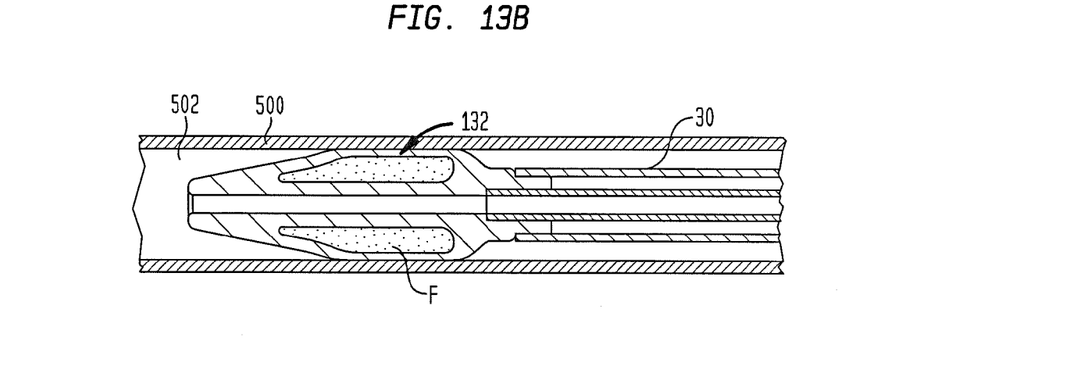
Figure 13C:
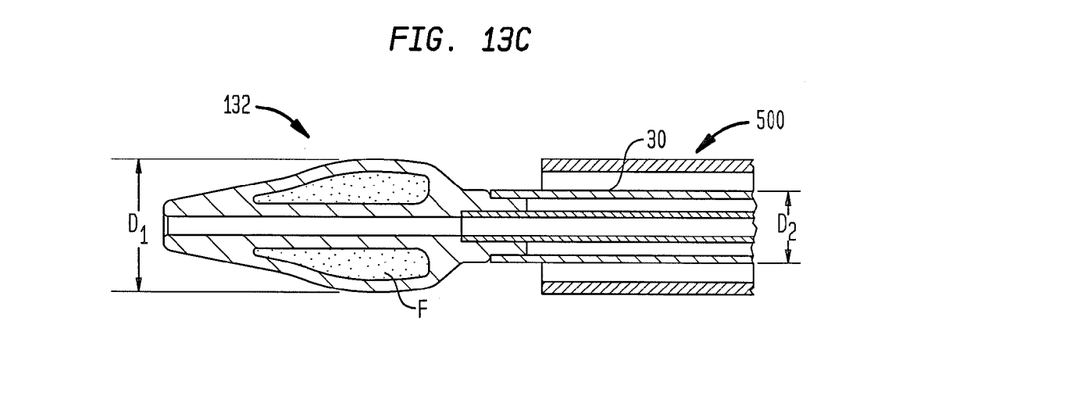

As seen in FIGS. 13A-13C, a delivery system with any of the tips described above can be used in conjunction with an introducer 500 to place a medical implant, such as a prosthetic heart valve, inside a patient. The introducer 500 may have a substantially cylindrical shape, and includes a longitudinal bore 502 sized and shaped to receive the delivery system. When the tip 132 is in the expanded condition, as shown in FIG. 13A, the maximum diameter $D_1$ of the tip is significantly larger than the outer diameter $D_2$ of the distal sheath 30 and larger than the inner diameter $D_3$ of the longitudinal bore 502 of the introducer 500.

To deliver a medical implant with the presently disclosed delivery system, the introducer 500 is first inserted inside a patient. The user may, for example, puncture the femoral artery using the Seldinger technique to access the patient's vasculature. The introducer 500 may then be inserted to provide a port through the patient's tissue to the femoral artery. The introducer 500 may be advanced through the femoral artery and a portion of the aorta, but does not necessarily reach the aortic arch. In one exemplary method, the introducer 500 may be advanced only through the femoral artery. A guidewire G may be inserted through the introducer 500 and advanced through the patient's vasculature until it reaches the desired site. The delivery system may then be inserted through the introducer 500, as seen in FIG. 13B, and advanced over the guidewire G. As the tip 132 is advanced through the longitudinal bore 502 of the introducer 500, the inner walls of the introducer exert compressive forces on the tip, radially compressing the tip so that its maximum diameter fits within the longitudinal bore. As seen in FIG. 13B, the shape of the tip 132 is changed to the compressed condition when the tip is positioned within the introducer 500. In the compressed condition, the maximum diameter $D_1$ of the tip 132 may be substantially similar to the inner diameter $D_3$ of the introducer 500, and similar to, or only slightly larger than, the outer diameter $D_2$ of the distal sheath 30.

Once the tip 132 and the distal sheath 30 of the delivery system are positioned within the introducer 500, the delivery system may be advanced distally toward the target site (e.g., the native aortic valve annulus). The delivery system may be moved distally relative to the introducer 500 until at least the tip 132 exits the distal end of the introducer. Once the tip 132 of the delivery system has exited the introducer 500, the tip is no longer subjected to the compressive forces exerted by the introducer and, therefore, it changes back to its expanded condition, as seen in FIG. 13C. In the expanded condition, the maximum diameter $D_1$ of the tip 132 is once again significantly larger than the outer diameter $D_2$ of the distal sheath 30.

As shown in FIG. 14, in the transfemoral delivery approach, the delivery system is advanced over the guidewire G through the aortic arch A in a retrograde manner. While passing through the aortic arch A, the distal sheath 30 and the tip 132 of the delivery system tend to follow a straighter path than the curve of the aortic arch and impinge upon the outside wall W of the arch. However, since the maximum diameter $D_1$ of the tip 132 is larger than the outer diameter $D_2$ of the distal sheath 30, the distal end 34 of the distal sheath 30 will be deflected away from the walls of the patient's vasculature and is unlikely to engage lesions or calcified tissue C thereon, including on the outside wall W of the aortic arch A.

In the transfemoral approach, the user may continue to advance the delivery system through the patient's vasculature until the tip 132 reaches the native aortic valve annulus. At this point, the distal sheath 30 may be moved proximally relative to the support shaft 28 to deploy a prosthetic heart valve supported on the support shaft. Before completing deployment of the prosthetic heart valve, the user may assess whether the valve is being deployed in the correct position. If an adjustment is necessary, the user may move the distal sheath 30 in a distal direction relative to the support shaft 28 to collapse and resheath the prosthetic heart valve. After repositioning the delivery system, the user may again move the distal sheath 30 proximally relative to the support shaft 28 to deploy the prosthetic heart valve at the correct target site.

When the user employs a delivery system with the tip 232 depicted in FIG. 10, the inner walls of the introducer 500 exert compressive forces on the tip when the tip is positioned within the introducer, thus maintaining the tip in the collapsed condition. As the delivery system is moved distally relative to the introducer 500, the tip 232 of the delivery system will eventually slide out from the distal end of the introducer. At this point, the porous outer portion 237 of the tip 232 will be exposed to large quantities of blood. As the porous outer portion 237 absorbs blood, it will expand to the expanded condition, as seen in FIG. 10. In the expanded condition, the maximum diameter $D_1$ of the tip 232 is larger than the outer diameter $D_2$ of the distal sheath 30, thereby inhibiting the distal end 34 of the distal sheath 30 from contacting the walls of the patient's vasculature. Such action is likely to prevent the distal end 34 from engaging lesions or calcified tissue C on the patient's vasculature.

When the user employs a delivery system with the tip 432 shown in FIG. 11, the user can actively expand the tip by injecting a fluid, such as saline, into the porous outer portion 437. In this exemplary method, the user may activate a fluid source coupled to the delivery system when the tip 432 is positioned distally of the introducer 500. Upon activation, the fluid source will supply a fluid to the porous outer portion 437 of the tip 432 via the conduits 460. As the outer portion 437 absorbs the fluid from the fluid source, it will expand to its expanded condition.

When the user employs a delivery system with the tip 332 illustrated in FIG. 12, the user can actively expand the tip by injecting a fluid, such as saline, into the inner cavity 338. In this exemplary method, the user may activate a fluid source connected to the delivery system when the tip 332 is located distally of the introducer 500. When the fluid source is activated, it will supply a fluid to the inner cavity 338 of the tip 332 via conduits 360 and, consequently, will expand the tip 332, as seen in FIG. 12.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery system for delivering and deploying a medical implant, comprising:
   an elongated support member configured to hold the medical implant;
   a sheath having an outer diameter surrounding at least a portion of the elongated support member, the sheath being movable in a longitudinal direction between a proximal position and a distal position relative to the elongated support member; and
   a tip attached to the elongated support member so as to overlap an end portion of the elongated support member, the tip being positioned at a distal end of the sheath when the sheath is in the distal position, the tip having an exterior surface, a closed inner cavity containing a fluid substance, a compressed condition, an expanded condition and a variable diameter along a length thereof, the variable diameter including a maximum diameter in the expanded condition, the maximum diameter being larger than the outer diameter of the distal end of the sheath, the tip including at least a first portion formed of a first solid material having a first stiffness and a second portion formed of a second solid material having a second stiffness different from the first stiffness such that a cross-section of the tip in a direction orthogonal to the longitudinal direction and at a spaced distance from the elongated support member passes through both the first portion and the second portion.

2. The delivery system of claim 1, wherein the tip is at least partly made of a compressible material selected from the group consisting of polyether block amide, polyurethane, and silicone rubber.

3. The delivery system of claim 1, wherein the fluid substance is selected from the group consisting of a liquid, a gel, and a gas.

4. The delivery system of claim 1, wherein the maximum diameter of the tip in the expanded condition is about 0.005 inches to about 0.020 inches larger than the outer diameter of the sheath.

5. The delivery system of claim 1, wherein the tip is molded over a portion of the elongated support member.

6. The delivery system of claim 1, further comprising a plurality of longitudinal recesses formed on the exterior surface of the tip along the length of the tip.

7. The delivery system of claim 1, wherein the tip includes an outer member formed from a porous material and an inner member formed from an elastic material.

8. The delivery system of claim 7, wherein the outer member surrounds at least a portion of the inner member.

9. The delivery system of claim 7, wherein the tip further includes an impermeable layer surrounding the outer member.

10. The delivery system of claim 1, wherein the tip is formed by an injection molding process.

11. The delivery system of claim 10, wherein the injection molding process is a multi-step injection molding process.

12. The delivery system of claim 10, wherein the injection molding process includes an overmolding step.

13. A delivery system for delivering and deploying a medical implant, comprising:
   an elongated support member configured to hold the medical implant;
   a sheath having an outer diameter surrounding at least a portion of the elongated support member, the sheath being movable between a proximal position and a distal position relative to the elongated support member; and
   a tip attached to the elongated support member and positioned at a distal end of the sheath when the sheath is in the distal position, the tip having an exterior surface, a closed inner cavity, a compressed condition, an expanded condition and a variable diameter along a length thereof, the variable diameter including a maximum diameter in the expanded condition, the maximum diameter being larger than the outer diameter of the distal end of the sheath; and a plurality of longitudinal recesses formed on the exterior surface of the tip along the length of the tip, the recesses being positioned circumferentially about the closed inner cavity so that a cross-section of the tip in a direction orthogonal to the longitudinal direction passes through the closed inner cavity and the plurality of recesses.

\* \* \* \* \*